Nov. 15, 1960 R. KORDES Plant Pat. 1,986
ROSE PLANT
Filed Feb. 4, 1960
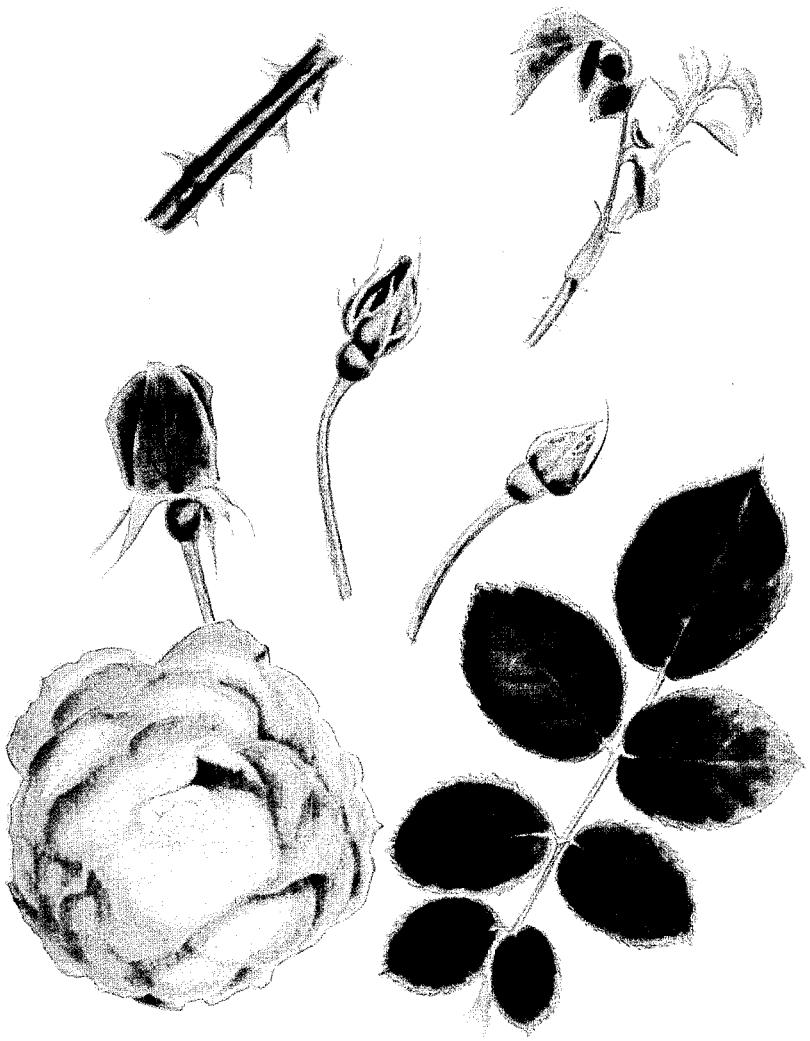
Inventor.
Reimer Kordes
By: Robb & Robb
Attorneys.

United States Patent Office

Plant Pat. 1,986
Patented Nov. 15, 1960

1,986

ROSE PLANT

Reimer Kordes, Barmstedt, near Elmshorn, Germany, assignor to Jackson & Perkins Company, Newark, N.Y., a corporation of New York Filed Feb. 4, 1960, Ser. No. 6,833

1 Claim. (Cl. 47—61)

The present invention relates to a new and distinct variety of rose plant of the floribunda class which was originated by me by crossing an unnamed and unpatented seedling derived from a cross of the unpatented "Ama" and "Rudolph-Timm," with the variety "Our Princess" (unpatented).

The primary objective of this breeding was to produce a new rose variety having medium growing and very free flowering habits and which bears red flowers of the floribunda type. This objective was fully achieved, along with other desirable improvements, as evidenced by the following unique combination of characteristics which are outstanding in the new variety and distinguish it from its parents, as well as from all other varieties of which I am aware:

(1) Symmetry of the plant and the flowers, with the flowers distributed uniformly over the plant;

(2) A free-flowering habit;

(3) A distinctive and non-fading deep velvety crimson general color tonality of the flowers, lightly overcast with Spectrum Red color; and (4) Unusual and distinctive "carrying power" of the flower color which can be very easily picked out from a long distance.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed seedling of "Ama" × "Rudolph Timm."

*Pollen parent.*—"Our Princess."

Classification:

*Botanic.*—Floribunda.

*Commercial.*—Floribunda.

*Flower*

(Observations made from specimens grown in a greenhouse at Newark, New York, U.S.A., in the latter part of the month of May.)

Blooming habit: Recurrent—continuous.

Bud:

*Size.*—Medium.

*Form.*—Ovoid; is not affected by wet or hot weather.

*Color.*—When sepals first divide—Burnt Lake, Plate 12. When petals begin to unfurl—Bordeaux, Plate 12. When half-blown: Inside of petals—Oxblood Red, Plate 1, lightly overcast with Carmine, Plate1; reverse of petals—Oxblood Red, Plate 1.

*Sepals.*—Branched; curl back when petals begin to unfurl. Color: inside—Pale Fluorite Green, Plate 32; outside—Jade Green, Plate 31.

*Calyx.*—Color—Jade Green, Plate 31. Shape—pear. Size—small. Aspect—smooth. Odor when rubbed—none.

*Peduncle.* — Length — medium. Aspect — rough. Strength—erect; slender. Color—Oil Green, Plate 5.

*Opening.*—Opens up well; is not affected by adverse weather conditions.

Bloom:

*Size.*—Medium. Average size when fully expanded—3 inches.

*Borne.*—Both singly and several together.

*Stems.*—Medium length; normal strength.

*Form (when first open).*—Cupped, Permanence—retains its form to the end, but outer petals curl back.

*Petalage.*—Double (full but open center). Number of petals under normal conditions—25.

*Color.*—Center of flower—Spectrum Red, Plate 1, with edges of petals Carmine, Plate 1. Outer petals—Carmine, Plate 1, lightly overcast with Scarlet Red, Plate 1, in the center of the petals. Base of petals (aiglet)—Deep Rose Pink, Plate 12. Inside of petals—Carmine, Plate 1, lightly overcast with Spectrum Red, Plate 1. Reverse of petals—Pomegranate Purple, Plate 12. General tonality from a distance—Carmine, Plate 1, lightly overcast with Spectrum Red, Plate 1.

*Discoloration.*—Non-fading. General tonality at end of first day—Carmine, Plate 1, lightly overcast with Spectrum Red, Plate 1. Second day—Carmine, Plate 1, lightly overcast with Spectrum Red, Plate 1. Third day—Carmine, Plate 1, lightly overcast with Spectrum Red, Plate 1.

Petals:

*Texture.*—Thick; is not affected by wet or hot weather.

*Appearance.*—Inside—velvety. Outside—satiny.

*Form.*—Oval.

*Arrangement.*—Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Small; many; regularly arranged around styles. Color—Capucine Yellow, Plate 3.

Stamens, filaments (threads): Medium length. Color—Light Chalcedony Yellow, Plate 17.

Pollen: Color—Pale Yellow-Orange, Plate 3.

Styles: Bunched; uneven length; short; thin.

Stigmas: Color—Apricot Yellow, Plate 4.

Ovaries: All enclosed in calyx.

Hips: None.

Seeds: None.

*Plant*

Form: Bush.

Growth: Vigorous; branching.

Foliage: Compound of 5 to 7 leaflets.

*Size.*—Large.

*Quantity.*—Normal.

*Color.*—New foliage: upper side—Lettuce Green, Plate 5, with edges Carmine, Plate 1; under side—

Yellowish Oil Green, Plate 5, lightly overcast with Hay's Russet, Plate 14. Old foliage: upper side—Cress Green, Plate 31; under side—Light Cress Green, Plate 31.

*Shape.*—Oval.

*Texture.*—Upper side—leathery. Under side—smooth.

*Ribs and veins.*—Ordinary.

*Edge.*—Serrated (saw-toothed).

*Serration.*—Single; small.

*Leaf stem.*—Color—Biscay Green, Plate 17. Under side—prickly.

*Stipules.*—Short; smooth.

Wood:

*New wood.*—Color—Lettuce Green, Plate 5. Bark—smooth.

*Old wood.*—Color—Dark Cress Green, Plate 31. Bark—smooth.

Thorns:

*Thorns.*—Quantity: on main stalks from base—many; on laterals from stalk—many. Form—narrow base; medium length; some straight and some hooked downward. Color (when young)—Brazil Red, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of symmetry of the plant and the flowers, with the flowers distributed uniformly over the plant, a free-flowering habit, a distinctive and non-fading deep velvety crimson general tonality of the flowers, with a light overcast of Spectrum Red, and the unusual and distinctive carrying power of the flower color which is detectable even at a long distance.

No references cited.